United States Patent [19]

Cambiaghi et al.

[11] Patent Number: 4,668,625
[45] Date of Patent: May 26, 1987

[54] PROCESS FOR PREPARING PEPTIDES

[75] Inventors: Stefano Cambiaghi, Pavia; Franco Dallatomasina, Segrate; Pietro Giardino, Milan; Enzo Murador, Melzo; Gaspare Spreafico, Pioltello, all of Italy

[73] Assignee: Farmitalia Carlo Erba, Milan, Italy

[21] Appl. No.: 638,494

[22] Filed: Aug. 7, 1984

[30] Foreign Application Priority Data

Jun. 27, 1984 [IT] Italy ................................ 21622 A/84

[51] Int. Cl.$^4$ .................. C12P 21/02; C12N 9/80; C12R 1/01; C12R 1/645
[52] U.S. Cl. ................................ 435/70; 435/228; 435/822; 435/911
[58] Field of Search .................. 435/70, 228

[56] References Cited

U.S. PATENT DOCUMENTS

| | | |
|---|---|---|
| 3,962,036 | 6/1976 | Liersch et al. ................... 435/228 X |
| 4,264,734 | 4/1981 | Kahan et al. ..................... 435/228 X |
| 4,293,648 | 10/1981 | Davino ................................ 435/70 |
| 4,302,540 | 11/1981 | Hirata et al. ..................... 435/280 X |
| 4,315,074 | 2/1982 | Royer ................................ 435/70 |
| 4,360,593 | 11/1982 | Konishi et al. .................... 435/70 |

OTHER PUBLICATIONS

Chemical Abstracts, vol. 99, 171860d (Svedas et al., Bioorg. Khim, 1983, 9(8), 1139–41).
Rossi et al., Farmaco. Ed. Sci., 1973, 28(3), 262–264.
Kameda et al., Chem. Pharm. Bull., 26(9), 2710–2717 (1978).
Brtnik et al., Collection Czechoslovak Chem. Commun., vol. 46, pp. 1983–1989 (1981).
Chemical Abstracts, vol. 90, (1979), p. 213, 50287c, Kameda et al.
Chemical Abstracts, vol. 96, 35705t (1982), pp. 713–714, Brtnik et al.
Chemical Abstracts, vol. 79, (1973), p. 108, 50210v, Rossi et al.

*Primary Examiner*—Lionel M. Shapiro
*Attorney, Agent, or Firm*—Oblon, Fisher, Spivak, McClelland & Maier

[57] ABSTRACT

The invention describes a process for preparing peptides. More particularly, a process for preparing L-α-aspartyl-L-phenylalanine $C_1$–$C_4$ lower alkyl ester is described and claimed by enzymatic hydrolysis of a suitable N-acyl-derivative.

20 Claims, No Drawings

PROCESS FOR PREPARING PEPTIDES

BACKGROUND OF THE INVENTION

1. Field of the Invention

The present invention refers to a process for preparing peptides. More particularly, the present invention refers to a process for preparing L-α-aspartyl-L-phenylalanine $C_1$–$C_4$ lower alkyl ester by enzymatic hydrolysis of a suitable N-acyl-derivative.

The invention relates also to the preparation of the well known sweetening agent having the generic name aspartame, by enzymatic hydrolysis of a suitable N-acyl-derivative.

DISCUSSION OF THE BACKGROUND

Aspartame, that is L-α-aspartyl-L-phenylalanine methyl esters, is very much used as a sweetening agent for goods and beverages with low calories. Its use is disclosed and claimed by the U.S. Pat. No. 3,492,131. Many improved processes for the production, extraction and purification of this substance have been disclosed and claimed.

It has been known from the literature a method which uses enzymes to remove N-amino protecting groups of aminoacids (for example, N-acyl substituted aminoacids) for the preparation and separation of L-amino acids, such as L-methionine, L-phenylalanine from the mixtures of the corresponding D,L-(N-acyl)-derivatives by using suitable enzymes, such as L-aminoacidacylasis from microbic origin or animal organs.

Enzymes are, in fact, proteic substances operating as very active catalysts in bioreactions which, in consideration of their very high specificity, are enormously much better than the catalysts or reagents commonly used in many chemical reactions.

It is not very well known to use enzymes to selectively catalyze the hydrolysis of N-protecting groups bonded to the terminal amino groups of peptides syntetized in different manners.

In fact, enzymes such as pepsin, chymotrypsin and proteases generally have either peptidic activity, that is they are able to hydrolyze peptidic bonds P-NH-CO-P′, wherein P and P′ represent aminoacid or peptide residues, or amidohydrolasic activity, that is they are able to hydrolyse the amidic bond A-CO-NH-P wherein P represents an aminoacid or peptide residue and A represents a residue of a carboxylic aromatic or aliphatic acid.

It is known, for instance, that an enzyme extracted from ox liver, defined as α-N-acylpeptide hydrolases, has been isolated by Gade and Brown (J. Biol. Chem. 253, 14, 5012–5018) and it is known to be active on acyltrialanine and other tri- and di-peptides with different rates. A very well known class of acylases defined penicillino-acylases is widely used industrially for preparing 6-amino-penicillanic acid (6-APA) by enzymatic hydrolysis of penicillins being different substituted with side alyphatic or aromatic chains to the amino group at the 6-position: these enzymes are classified as penicillin-acylases acting on penicillins G-V-X-F etc. according to the differents properties of the substituents to be hydrolyzed.

In the specific field of the preparation of aspartame the chemical enzymatic synthesis of N-acyl-L-α-aspartyl-L-phenylalanine methyl ester is carried out starting from acyl-L-aspartyl derivatives and L-phenylalanine methyl ester.

N-acyldipeptide, such obtained, is then usually hydrolyzed chemically, for instance by hydrochloric hydrolysis, to obtain the final desired compound, that is L-α-aspartyl-L-phenylalanine methyl ester. However, the process of chemical hydrolysis has several disadvantages consisting, especially, in its aspecificity and subsequent formation of undesired compounds due either to the peptide hydrolysis reactions with formation of aspartic and and phenylalanine derivatives or to ester hydrolysis reactions with formation of demethylated aspartames or, finally, to cyclizing reactions with formation of diketopiperazines differently substituted.

The presence of all these by-products, beside lowering the production yields, makes difficult the extraction phases to obtain the desired compound at the desired degree of purity and requires further chemical and biochemical processes to recover the important by-products of the reaction so as to optimize the process from an economic point of view.

SUMMARY OF THE INVENTION

An object of the present invention is a process of enzymatic hydrolysis of N-acyl-aspartame characterized by using an hydrolase (an enzyme possessing hydrolytic activity). Particularly, the process disclosed and claimed herein allows to obtain, under conditions remarkably simpler than those used in the chemical hydrolysis, a final product, aspartame, in very high yields and with a drastic reduction of the quantity of undesired by-products.

DETAILED DESCRIPTION OF THE PREFERRED EMBODIMENTS

Hydrolases suitable for the present process are, for example, acid or neutral proteases which under appropriate conditions hydrolyze the amidic bond of an N-acyl-peptide with the formation of the desired peptide.

Particularly, preferred hydrolases for the process of enzymatic hydrolysis of N-acyl-aspartame are deacylating enzymes obtained from microbal strains of Escherichia, Nocardia, Proteus, Penicillium or Streptomyces genus commonly classified as acylases and more specifically as Penicillin-acylases.

The hydrolytic process can be carried out either by using directly the free or immobilized microbic cells or by isolating the specific enzymes which can be used in the free form or immobilized according to known techniques to resins, glass cellulose or similar substances by ionic or covalent bonds or grafted to fibers permeable to the substrate. The use of the enzymes isolated and purified at the desired degree is preferred rather than the raw cellular extract since the extraction or purification process normally allows to reduce or eliminate the presence of contaminated enzymes causing a lowering of enzymatic process yields with formation of undesired by-products.

According to the present invention, therefore, the deacylation of N-substituted peptide is preferably performed by treating this compound in an aqueous medium with an enzymatic preparation displaying acylases activity.

More preferably, the process claimed herein deacylates a N-substituted derivative of L-α-aspartyl-L-phenylalanine methyl ester with an enzyme isolated and purified and having acylase activity.

As already above mentioned, the preferred hydrolyses used according to the present invention, either in the soluble form or immobilized to a suitable inert substrate or insolubilized by a cross-linkage process, are those classified as acylases and up to now mostly known as penicillinacylases.

Some examples of these enzymes are: fungus origin acylases produced by fermentation of various species of antinomycetes, filamentous fungi and yeasts, such as for example:

| | |
|---|---|
| Alternatia | Mucor |
| Aspergillus | Penicillium |
| Botrytis | Phoma |
| Cephalosporium | Streptomyces |
| Cryptococcus | Trichoderma |
| Emericellopsis | Trichophyton |
| Epicoccum | Trichosporon |
| Epidermophyton | Actinoplanes |
| Fasarium | Nocardia | or bacterium origin acylases produced by fermentation of various bacteric species such as:

| | |
|---|---|
| Aerobacter | Flavobacterium |
| Alcaligenes | Micrococcus |
| Bordetella | Proteus |
| Cellulomonas | Pseudomonas |
| Corynebacterium | Salmonella |
| Erwinia | Sarcina |
| Escherichia | Xanthomonas |
| B. megaterium | B. subtilis |
| Achromobacter | |

Also enzymatic preparations obtained by extraction of animal organs, such as pig-kidney acylases are able to cause hydrolysis of the amide bond between the carbonyl group of an organic acid and the amine group of L-aspartyl-L-phenylalanine methyl ester. Aspartame, that is L-αaspartyl-L-phenylalanine methyl ester has been up to now prepared by chemical condensation of L-phenylalanine methyl ester with an active form of L-aspartic acid N-substituted with an organic acid residue, such as formic acid, acetic acid or others (U.S. Pat. No. 3,786,039); it is also known an enzymatic synthesis between L-phenylalanine methyl ester and a N-substituted L-aspartic acid derivative (U.S. Pat. No. 4,284,721) such as benzyloxycarbonyl, butyloxycarbonyl etc., carried out in a non-aqueous medium with an enzyme named as metalproteinases.

The intermediate product obtained either by chemical process or by enzymatic synthesis, that is N-substituted L-α-aspartyl-L-phenylalanine methyl ester, can be isolated from the reaction mixture either by concentration up to crystallization, by extraction or by other procedures. The compound is then hydrolysed to remove the N-protecting group so obtaining L-α-aspartyl-L-phenylalanine methyl ester having edulcorating properties 200 times higher than those of saccharose.

The known processes used to remove the N-protecting groups consist mainly in acid or basic chemical hydrolysis. For example, the N-deprotection is carried out either in the presence of a strong acid (U.S. Pat. No. 4,071,511) or in the presence of bases, such as hydroxylamine or acetyl hydrazine (U.S. Pat. No. 4,021,418 and U.S. Pat. No. 4,434,097).

As previously mentioned, these chemical deacylating processes have many disadvantages from an industrial point of view, such as for example low yields, expensive reagents in addition to the fact that the obtained product must be purified repeatedly to eliminate the various by-products caused by esterification of the free carboxy group or by hydrolysis of the ester or of the peptide bond.

The disadvantages and the limits of the chemical hydrolysis of the N-protecting group of dipeptide alkylesters, such as L-α-aspartyl-L-phenylalanine methyl ester, are overcome by the enzymatic hydrolysis according to the method of the present invention.

The preferred enzymes having a deacylating activity are produced by microorganisms such as Penicillium, Streptomyces, Aspergillus, Escherichia Coli, Nocardia, Proteus, purified with peculiar methods to remove the undesidered enzymatic activities, for instance the esterase activity which would act on the product to be hydrolysed, that is the N-substituted L-α-aspartyl-L-phenylalanine methyl ester, to obtain demethylated aspartame.

The above enzymes are immobilized by suitable methods to resins or other suitable substrates in order to economize the process by using the same immobilized ebzyme for many preparation cycles.

The same results above described can be obviously obtained by using the enzyme in the non immobilized form.

The enzymes thus prepared and selected are added to aqueous solution or mildly buffered at different pH according to the enzyme used, that is in a range of from 2 to 9, preferably from 5 to 7, and in the presence of an aspartame N-acyl derivative, at the concentration of from 0.2 to 260 g/l, having the following formula (I):

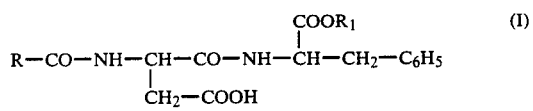

wherein R represents hydrogen or a free or substituted alkyl, alkenyl or phenylalkyl group having from 1 to 11 carbon atoms, selected from the group consisting of —CH$_3$, —(CH$_2$)$_n$CH$_3$ wherein n is a number from 1 to 10, —C$_6$H$_5$, —CH$_2$—C$_6$H$_5$, —CH$_2$—C$_6$H$_4$—OH, —CH$_2$—C$_6$H$_4$—NO$_2$, —C$_6$H$_3$(OCH$_3$)$_2$, —CH$_2$—C$_6$H$_3$(OH)$_2$, —CH$_2$—CH=CH—CH$_2$—CH$_3$—CH$_2$—S—CH=CH$_2$, —CH$_2$—O—R' wherein R' is selected from the group consisting of —C$_6$H$_5$, —CH$_3$, —(CH$_2$)$_m$—CH$_3$ wherein m=1:5, —C$_6$H$_4$—CH$_3$, —C$_6$H$_4$—OH; and R$_1$ is a C$_1$–C$_4$ lower alkyl. The reaction is carried out at a temperature of from 10° to 60° C., preferably 15°–40° C., for 1 to 48 hours operating in batch or column according to the quantity of the enzyme present in the reaction mixture and to the ratio between the quantity of the enzyme in solution or in the immobilized from the quantity of N-substituted dipeptide present in the reaction mixture.

The yields of the reactions carried out under optimal conditions reach values higher than 80% making superfluous the complicated and expensive processes for recovering the unreacted compounds or the undesired by-products, which are commonly necessary when the hydrolysis reaction of the aspartame N-protecting group is carried out with a chemical process.

Aspartame thus obtained is extracted according to the known technical procedures.

The following examples and preparations illustrate the invention without limiting its scope.

The N-acyl derivatives which preparation is not specifically indicated, were obtained in high yields by operating as described in the preparation A, B, C and D and using a suitable acylating derivative as starting material.

Preparation A

N-Phenylacetyl-L-αβ-aspartyl-L-phenylalanine methyl ester 66.6 g of L-aspartic acid were suspended in 100 ml of $H_2O$. 10% NaOH (200 ml) were added and the mixture was cooled to 15°–17° C.; a solution of 10% NaOH (100 ml) and phenylacetylchloride (70 ml) has been dropped therein for 1 hour contemporaneously.

The mixture was kept 3 hours at 20° C. and then added with 37% hydrogen chloride up to pH 2.

After cooling to 0°–5° C. and filtration the reaction mixture was dried to obtain N-phenyl acetylaspartic acid (120 g), 99.77% titer. 78 g of N-phenylacetyl aspartic acid were suspended in 80 ml of acetic anidride. The mixture was heated to 80° for 2 hours. 70 g of N-phenylacetyl aspartic anhydride were obtained after cooling and insolubilization with a solvent. 52 g of N-phenylacetyl aspartic anhydride suspended in 52 ml of glacial acetic acid and 100 ml of dichloroethane cooled to 10° C. were added with 200 ml of dichloroethane containing 40.2 g of phenylalanine methyl ester.

85 g of the title compound were obtained after extractions with base adjusting the pH to acid value and filtration.

Preparation B

N-phenoxy-L-α-aspartyl-L-phenylalanine methyl ester

Operating as described in the Preparation A, but starting from 77.2 g of phenoxy-acetyl chloride instead of phenyl-acetyl chloride, 110 g of the title compound were obtained.

Preparation C

N-p-hydroxyphenylacetyl-L-αβ-aspartyl-L-phenylalanine methyl ester

Operating as described in the Preparation A, but starting from 60.4 g of p-hydroxyphenylacetyl chloride, 70.7 g of the title compound were obtained.

Preparation D

N-propionyl-L-αβ-aspartyl-L-phenylalanine methyl ester

Operating as described in the Preparation A, but starting from 41.8 g of propionyl chloride instead of phenylacetyl chloride, 33,8 g of the title compound were obtained.

The acylases compounds were prepared by fermentation with above mentioned miroorganisms in specific culture broths.

Preparation E

Acylases from E. Coli ATCC 11105

The microorganism was fermented in a culture broth consisting of yeast extract, sodium glutammate, phenylacetic acid, ammonia salts, buffered so as to guarantee an initial pH of 6.8–6.9.

The optimal growth was reached in 10–12 hours with cellular dried weight of 300–400 mg/100 ml of broth.

When the fermentation was over, the cells were separated by centrifugation, washed and passed on to a lysis treatment with n-butyl-acetate.

The lysate compound was flocculated, clarified and ultrafiltered. The concentrate obtained by selective ultrafiltration was salted with $(NH_4)_2SO_4$.

The salted compound consisted of a stable acylases having an activity of 600–900 U/ml.

EXAMPLE 1

2 g of N-phenylacetyl-L-aspartyl-L-phenylalanine methyl ester (obtained in the Preparation A) was dissolved in 100 ml of water with progressive additions of 10% NaOH, keeping the mixture under shaking at 37° C. and at a pH lower than 7.5. When the solution was over, 1N NaOH or 1N HCl was added to stabilize the pH value at 6.5–6 and the mixture was added with 0.5 g of the enzyme compound having an acylase activity of 50 U/g, obtained by immobilization of the compound of Preparation E on a solid substrate, by selective adsorbtion and Cross-linkage with glutaraldehyde, in the presence of albumin.

The reaction mixture was allowed to react for 23 hours, heated to 37° C., under shaking, and the pH was kept at 6±0.5 by addition of 1N NaOH; at the end of the reaction the immobilized enzyme is separated by filtration, in vacuo, through a glass filter and washed with 100 ml of water.

The filtrate and the washing liquors were combined and the solution was analysed by high pressure liquid chromatography (HPLC) indicating a hydrolysis yield of phenylacetyl-L-α-aspartyl-L-phenylalanine methyl ester of 90% of the theoric value, only 5% of the non reacted compound and 5% of undesired products.

The obtained aspartame was then extracted and crystallized according to suitable preparation processes from low salt containing aqueous solutions, and the free phenylacetic acid was recovered by extraction with solvents or adsorbtion on resins and used again for further preparations.

EXAMPLE 2

2 g of N-phenoxyacetyl-L-aspartyl-L-phenylalanine methyl ester obtained in the preparation B was dissolved in 100 ml of water heated to 35° C. with addition of 10% NaOH and keeping the pH not higher than 7.5. After solubilization the pH was adjusted to 6.0 and 0.5 g of Novozym acylases 217 at 60 U/g were added being the enzyme immobilized to a suitable insoluble substrate.

The mixture was allowed to react for 24 hours at 35° C., under shaking and maintaining the pH at 6±0.5 with addition of 1N NaOH; the immobilized enzyme was then recovered by filtration through glass filter and washed with 10 ml of water.

The filtrate and the washing liquors were combined and the solution is chromatographied (HPLC) obtaining a yield of 93% of the theoric value.

EXAMPLE 3

The reaction is carried out as described in Example 1, except for the enzyme is adsorbed on an ion exchange resin and insolubilised by cross-linkage in the presence of gluteraldehyde and a diamine according to known methods (Haynes R.; Biochem. Biophys. Res. Commun 36, 235 (1969)). The compound having 16 U/g was used at the quantity of 2 g per 100 ml of 2% solution of N-phenylacetyl-L-aspartyl-L-phenylalanine methyl ester. Reaction yields were 80% after 22 hours of reaction.

EXAMPLE 4

The reaction is carried out as described in Example 1, except for the enzyme was insolubilized by grafing on cellulose acetate fibers according to known processes (Dinelli D., Process Biochem 718,9,1972). The compound had 10.000 U/g and 1 g of fiber was used to obtain 90% of transformation at the conditions mentioned in the Example 1.

EXAMPLE 4 Bis

The reaction is carried out as described in Example 1, except for the enzyme was insolubilized on porous glass particles with primary amine functions by activation with gluteraldehyde and a covalent bond of the enzyme on the carbonylic intermediate.

The compound had 25 U/g and 2 g of the immobilized enzyme was used to obtain 75% of transformation at the conditions described in the Example 1.

EXAMPLE 5

The reaction is carried out described in the Example 1, except for the enzyme of preparation E was used in the soluble form. 100 ml of a 2% solution of N-phenylacetyl-L-aspartyl-L-phenylalanine methyl ester were added with 160 U of enzyme extracted from culture broths of E. Coli. The reaction mixture was maintained for 8 hours at 37° C. and pH 6–6.5 reaching at these condition a yield of the desired product of 87% of theoric value.

EXAMPLE 6

3 g of N-p-hydroxyphenylacetyl-L-aspartyl-L-phenylalanine methyl ester (obtained in preparation C) were dissolved in 100 ml of water, the pH was adjusted to 6 and the solution was heated to 40° C. and then added with 1 g of acylases (penicillinacylases) from E. Coli adsorbed on an ion exchange resin and having the activity of 40 U/g.

The reaction mixture was kept under shaking, at 40° C., at pH 5.5–5.6 for 20 hours: the immobilized enzyme was then separated by filtration, the reaction mixture by chromatographic analyzed (HPLC) shows a quantity of aspartame produced by the enzymatic hydrolysis of 82% of the theoric value.

EXAMPLE 7

As described in the Example 6, except for the used enzyme was obtained by extraction of the culture broth of Nocardia and used in the soluble form.

By carrying out the reaction at the described conditions, N-p-hydroxyphenylacetyl-L-aspartyl-L-phenylalanine methyl ester was transformed into aspartame with a yield of 50% of the teoric value.

EXAMPLE 8

As described in Example 1, except for the immobilized enzyme used was obtained by extraction from a culture broth of Proteus, having an activity of 25 U/g and was used in a quantity of 1 g/100 ml of the reaction mixture.

The aspartame yield obtained under these conditions was 48% of the theoric value.

EXAMPLE 9

3 g of N-propionyl-L-aspartyl-L-phenylalanine methyl ester obtained according to the preparation D were dissolved in 100 ml of water, the solution heated to 37° C. and the pH adjusted to 6.5.

The reaction mixture was added with 300 U/g of the enzymatic compound obtained by extraction and purification according to the known methods of the culture broth of E. coli.

The reaction mixture was kept under shaking for 24 hours at the indicated temperature, keeping the pH at 6.5±0.5: the final yield of aspartame is higher than 40% of the theoric value.

EXAMPLE 10

Operating as described in Example 9, but substituting N-propionyl-L-aspartyl-L-phenylalanine methyl ester with an enzymatic compound having acylase activity which was reacted at pH 6±1 on a solution containing 0.5 g/l of N-undecylcarbonyl-L-aspartame; hydrolysis yields of 30% of the theoric value.

EXAMPLE 11

2 g of N-formyl-L-aspartyl-L-phenylalanine methyl ester were dissolved in 100 ml of water heated to 37° C.

When solution was complete, the pH was adjusted to 6.5–7 with 10% NaOH, 250 U of an enzymatic compound having acylase activity obtained from Pseudomonas colture was added. The reaction mixture was allowed to stand for 36 hours at 37° C. The pH was then adjusted to 4–4.5 and the compound was separated by concentration. The yield of L-α-aspartyl-L-phenylalanine methyl ester is 20% of the theoric value.

EXAMPLE 12

Operating as in Example 2, except for the enzyme having 18.000 U/g extracted from broth culture of Aspergillus was used at a concentration of 2% of that of N-phenoxymethyl-L-aspartame, with hydrolysis yield of 20% of the theoric value.

EXAMPLE 13

As described in Example 1, except for the enzyme was not isolated, but the cells are immobilized "in toto": 1 g of humid cells obtained from E. Coli culture was suspended in 5 ml of buffer phosphate 50 mM, pH 7.5.

The solution was added with 0.5% of bovine albumin and 1% of glutaraldehyde. After 2 hours at room temperature the obtained pellets were separated by filtration and washed with buffer phosphate 50 mM. The compound used had an activity of 14 U/g and was used in a quantity of 2 g per 100 ml of a 2% solution of N-phenylacetyl-L-aspartyl-L-phenylalanine methyl ester.

The transformation yields after 8 hours of incubation at 37° C. were 65% of the theoric value.

EXAMPLE 14

As described in Example 2, except for the enzyme was not isolated and the mycelium mass obtained from a Streptomyces colture was immobilized. The linkage process was analogous to that described in Example 13. The cross-linked mycelium mass was separated by filtration, washed with water and liophilyzed. The liophilyzed compound was roughly triturated and used for the selective hydrolysis of N-phenoxyacetyl-L-aspartyl-L-phenylalanine methyl ester. 2 g of the compound having an activity of 12 U/g was used per 100 ml of 2% solution of the product to be hydrolysed.

The transformation yields after 8 hours of incubation at 37° C. are 60% of the theoric value.

EXAMPLE 15

1 g of N-propoxy-acetyl L-aspartyl-L-phenylalanine methyl ester was added to 100 ml of water heated to 37° C.

The product was dissolved adjusting the pH to 6 with 10% NaOH. The reaction mixture was added with 250 U of the enzymatic compound having acylase activity obtained from Cephalosporium colture. The mixture was allowed to stand for 20 hours at 37° C. At the end of the enzymatic reaction the yield was 45% of the theoric value.

EXAMPLE 16

1 g of N-tolyloxyacetyl-L-aspartyl-L-phenylalanine methyl ester was dissolved in 100 ml of H$_2$O and added progressively with 10% NaOH up to pH 6-7. The mixture was added with 250 U of enzymatic compound having acylase activity obtained from Actinoplanes Utahensis cultures. The reaction was carried out at 37° C. for 24 hours. The hydrolysis yield of the N-tyloxymethyl deerivative is 40% of the theoric value.

What we claim is:

1. A process for preparing a L-α-aspartyl-L-phenylalanine C$_1$-C$_4$ lower alkyl ester, comprising:
   (i) contacting an N-acyl derivative of formula (I):
   R—CO—NH—CH(CH$_2$COOH)—CO—NH—CH(CH$_2$C$_6$H$_5$)—COO—R$^1$ with a penicillin acylase, wherein R is an unsubstituted C$_1$-C$_{11}$ alkyl group, a substituted C$_1$-C$_{11}$ alkyl group, an unsubstituted C$_1$-C$_{11}$ alkenyl group, a substituted C$_1$-C$_{11}$ alkenyl group, an unsubstituted phenylalkyl group containing up to 11 carbon atoms, or a substituted phenylalkyl group containing up to 11 carbon atoms, and R$^1$ is a C$_1$-C$_4$ alkyl group; and
   (ii) isolating a L-α-aspartyl-L-phenylalanine lower ester.

2. A process for preparing a L-α-aspartyl-L-phenylalanine methyl ester, comprising:
   (i) contacting an N-acyl derivative of the formula:

R—CO—NH—CH(CH$_2$COOH)—CO—NH—CH(CH$_2$C$_6$H$_5$)—COO—CH$_3$ with a penicillin acylase, wherein R is a unsubstituted C$_{1-11}$ alkyl group, a substituted C$_{1-11}$ alkyl group, an unsubstituted C$_{1-11}$ alkenyl group, a substituted C$_{1-11}$ alkenyl group, an unsubstituted phenylalkyl group containing up to 11 carbon atoms, or a substituted phenylalkyl group containing up to 11 carbon atoms, and
   (ii) isolating L-α-aspartyl-L-phenylalanine methyl ester.

3. The process of claim 2, comprising using a N-acyl derivative in which R is selected from the group consisting of hydrogen, —CH$_3$, —(CH$_2$)$_n$CH$_3$ wherein n is from 1 to 10, —C$_6$H$_5$, —CH$_2$—C$_6$H$_5$, —CH$_2$—C$_6$H$_4$—OH, —CH$_2$—C$_6$H$_4$—NO$_2$, —C$_6$H$_3$(OCH$_3$)$_2$, —CH$_2$—C$_6$H$_3$(OH)$_2$, —CH$_2$—CH=CH—CH$_2$—CH$_3$, —CH$_2$—S—CH$_2$—CH=CH$_2$, and —CH$_2$—O—R' wherein R' is selected from the group consisting of —C$_6$H$_5$, —CH$_3$, —(CH$_2$)$_m$—CH$_3$ where m=1 to 5, —C$_6$H$_4$—CH$_3$, and —C$_6$H$_4$—OH.

4. The process of claim 1, comprising using a penicillin acylase prepared from a microorganism.

5. The process of claim 4, wherein the said microorganism is selected from the group of actinomycetes, fungi and bacteria.

6. The process of claim 5, wherein the said actinomycetes used is of the Nocardia, Actinoplanes or Streptomyces genus.

7. The process of claim 5, wherein the said fungi is of the Alternatia, Aspergillus, Botrytis, Cephalosporium, Cryptococcus, Emericellopsis, Epicoccum, Epidermophyton, Fusarium, Mucor, Penicillium, Phoma, Trictoderma, Trichophyton, or Trichosporon genus.

8. The process of claim 5, wherein the said bacteria is the Aerobacter, Alcaligenes, Bordetella, Cellulomonas, Corynebacterium, Erwinia, Escherichia Achromobacter, Flavobacterium, Micrococcus, Proteus, Pseudomonas, Salmonella, Sarcina, Xanthomonas, or *B. subtilis* genus.

9. The process of claim 1, comprising carrying out the reaction either in the presence of microorganism cells producing the penicillin acylase or by preparing the penicillin acylase separately and then using it on the compound of formula (I).

10. The process of claim 9, comprising using a penicillin acylase prepared separately and which has been isolated and purified.

11. The process of claim 9, wherein the said microbial cell or the penicillin acylase separately prepared, are either immobilized on an inert substrate or insolubilized by cross-linking.

12. The process of claim 5, comprising carrying out the hydrolysis of the said N-acyl derivatives of formula (I) in an aqueous solution at a concentration of from 0.2 to 260 g$^{-1}$, buffered at pH from 2 to 9, and at a temperature of from 10° to 60° C.

13. The process of claim 12, comprising using a pH of from 5 to 7 and a temperature of from 15° to 40° C.

14. The process of claim 1, comprising obtaining L-α-aspartyl-L-phenylalanine ester from N-phenylacetyl-L-α-aspartyl-L-phenylalanine methyl ester.

15. The process of claim 1, comprising obtaining L-α-aspartyl-L-phenylalanine methyl ester from N-phenoxyacetyl-L-aspartyl-L-phenylalanine methyl ester.

16. The process of claim 1, comprising using a penicillin acylase adsorbed on an ion-exchange resin and insolubilized by cross-linking.

17. The process of claim 1, comprising using a penicillin acylase grafted onto cellulose acetate fibers.

18. The process of claim 1, comprising using a penicillin acylase insolubilized onto porous glass.

19. The process of claim 1, comprising obtaining L-α-aspartyl-L-phenylalanine methyl ester from N-p-hydroxyphenylacetyl-L-aspartyl-L-phenylalanine methyl ester.

20. The process of claim 1, comprising obtaining L-α-aspartyl-L-phenylalanine methyl ester from N-propionyl-L-aspartyl-L-phenylalanine methyl ester, N-formyl-L-aspartyl-L-phenylalanine methyl ester, N-propoxy-acetyl-L-aspartyl-L-phenylalanine methyl ester, or N-tolyloxyacetyl-L-aspartyl-L-phenylalanine methyl ester.

* * * * *